(12) United States Patent
Brosette et al.

(10) Patent No.: US 8,718,947 B2
(45) Date of Patent: *May 6, 2014

(54) METHOD FOR MEASURING THE INCIDENCE OF HOSPITAL ACQUIRED INFECTIONS

(75) Inventors: Stephen E. Brosette, Vestavia, AL (US); Patrick A. Hymel, Jr., Vestavia, AL (US); Gerald T. LaBorde, Jr., Homewood, AL (US)

(73) Assignee: Carefusion 303, Inc., San Diego, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 13/272,158

(22) Filed: Oct. 12, 2011

(65) Prior Publication Data

US 2012/0029944 A1   Feb. 2, 2012

Related U.S. Application Data

(60) Continuation of application No. 11/939,619, filed on Nov. 14, 2007, now Pat. No. 8,060,317, which is a division of application No. 11/189,394, filed on Jul. 26, 2005, now Pat. No. 8,060,315.

(60) Provisional application No. 60/591,561, filed on Jul. 27, 2004, provisional application No. 60/678,899, filed on May 6, 2005.

(51) Int. Cl.
*G01N 33/48* (2006.01)

(52) U.S. Cl.
USPC .......................................................... 702/19

(58) Field of Classification Search
USPC .......................................................... 702/19
See application file for complete search history.

(56) References Cited

U.S. PATENT DOCUMENTS

2002/0116219 A1   8/2002   Ibok et al.

FOREIGN PATENT DOCUMENTS

JP   07-206603   8/1995
RU   2080601     5/1997

OTHER PUBLICATIONS

E. Meyer et al. Antibiotic Use and Resistance Surveillance in Germany (SARI). Infection 2003; 31: 208-215.*
Agvald-Ohman, C. et al, "Multiresistant coagulase-negative staphylococci disseminate frequently between intubated patients in a multidisciplinary intensive care unit", Critical Care, Feb. 2004, vol. 8, No. 1, ISSN 1364-8535, XP02101225.
Briassoulis, G. et al, "Prior antimicrobial therapy in the hospital and other predisposing factors influencing the usage of antibiotics in a pediatric critical care unit", Annuals of Clinical Microbiology and Anitmicrobials, Apr. 17, 2004, ISSN 1476-0711, XP021008027.
Gastmeier, P. et al, "Catheter-Associated Primary Bloodstream infections: Epidemiology and Preventive Methods", Infection 27, MMV Munchen, 1999.

* cited by examiner

*Primary Examiner* — Michael Borin
(74) *Attorney, Agent, or Firm* — McDermott Will & Emery LLP

(57) ABSTRACT

A method of determining an Antibiotic Utilization Criteria (AUC) marker includes assigning an AUC=1 to a patient if certain criteria are met: (1) antimicrobials were first dispensed to the patient after an initial number of days has passed since the patient's admission to a hospital, and either (2a) the antimicrobials were dispensed to the patient for a determined number of consecutive days after the day of first dispense, or (2b) the antimicrobials were dispensed to the patient on consecutive days after the day of first dispense up to and including the day on which the patient either was discharged or died. If criteria (1) is not satisfied or both of alternate criteria (2a) and (2b) are not satisfied, an AUC=0 is assigned to the patient.

9 Claims, 3 Drawing Sheets

METHOD FOR MEASURING THE INCIDENCE OF HOSPITAL ACQUIRED INFECTIONS

I. CROSS REFERENCE TO RELATED PATENT APPLICATIONS

This application is a continuation of U.S. application Ser. No. 11/939,619, filed on Nov. 14, 2007 and now issued as U.S. Pat. No. 8,060,317, which is a divisional application of U.S. application Ser. No. 11/189,394, filed on Jul. 26, 2005 and now issued as U.S. Pat. No. 8,060,315, which claims priority to U.S. Provisional Application No. 60/591,561 filed Jul. 27, 2004 and U.S. Provisional Application No. 60/678,899 filed May 6, 2005, all of which are herein incorporated by reference in their entireties.

II. BACKGROUND

A "hospital-acquired infection" is a localized or systemic condition that results from an adverse reaction to the presence of an infectious agent(s) or its toxin(s) and that was not present or incubating at the time of admission to the hospital. Hospital-acquired infections affect about 2,000,000 patients per year in the U.S., causing about 90,000 deaths. They are the fourth leading cause of death in the U.S., behind only cancer, strokes, and heart disease. In addition to their human toll, each infection costs nearly $14,000 to treat, totaling $28 B each year in the U.S.

Consumers, employers, hospital insurers, regulatory agencies and others wish to know how many infections occur and how many people acquire an infection occur each year in a given hospital. However, few hospitals can answer these questions.

The current state of the art for identifying hospital-acquired infections is advanced by the Centers for Disease Control and Prevention (CDC) through its National Nosocomial Infection Surveillance (NNIS) program. Under NNIS, there are 13 major site categories and 48 specific sites or types of infection for which criteria have been developed, (Garner et al., *APIC Infection Control and Applied Epidemiology: Principles and Practice*, 1996). The method requires specially trained hospital clinical personnel to manually review clinical and other data for each patient, including patient admission, transfer and discharge data, laboratory results, pharmacy data, radiology data, physician notes, and nursing notes for each patient.

Here is an example of one of the forty-eight infection criteria:
DEFINITION: Other infections of the urinary tract must meet at least one of the following criteria:
Criterion 1: Patient has organisms isolated from culture of fluid (other than urine) or tissue from affected site.
Criterion 2: Patient has an abscess or other evidence of infection seen on direct examination, during a surgical operation, or during a histopathologic examination.
Criterion 3: Patient has at least two of the following signs or symptoms with no other recognized cause: fever (>38° C.), localized pain, or localized tenderness at the involved site and at least one of the following:
a) Purulent drainage from affected site;
b) Organisms cultured from blood that are compatible with suspected site of infection;
c) radiographic evidence of infection, e.g., abnormal ultrasound, CT scan, magnetic resonance imaging (MRI), or radiolabel scan (gallium, technetium);
d) Physician diagnosis of infection of the kidney, ureter, bladder, urethra, or tissues surrounding the retroperitoneal or perinephric space; or
e) Physician institutes appropriate therapy for an infection of the kidney, ureter, bladder, urethra, or tissues surrounding the retroperitoneal or perinephric space.

This current state of the art for identifying hospital-acquired infections is a manual process that is so time consuming that no hospital has the personnel required to apply it to all patients in the hospital. Each patient admission requires at least 20 minutes to determine if a hospital-acquired infection was present, (Gavin P J, et al., *SHEA* 2004). At that rate, a hospital with 20,000 yearly admissions would require five full time trained reviewers just to measure the hospital's infection rate. Very few hospitals have this level of staffing for Infection Control.

In response to the lack of resources required to apply the NNIS method to all patients within most hospitals, the NNIS program eliminated the "hospital-wide component" (the calculation of the incidence of hospital-acquired infections throughout the hospital) in January 1999, (National Nosocomial Infections Surveillance (NNIS) System Report. *Am J Infect Control* 1999). As a result, most hospitals only identify certain infections in a subset of patients at certain times of the year. With this limited perspective, hospitals cannot determine the full extent of the problem of hospital-acquired infections nor its financial impact.

Moreover, the current manual process includes many criteria that require the subjective judgment of hospital clinical staff. In the 20+ years that the NNIS method has been used, there has been only one study regarding its objectivity, (Emori, et al., *Infect Control Hosp Epidemio.1* 1998). That study compared the number of infections reported from the same 1,136 patient charts when reviewed by three groups: NNIS participating hospitals, CDC-trained expert reviewers and CDC epidemiologists. The number of infections found by the three groups looking at the same 1,136 patient charts were 611, 1264 and 865, respectively. Moreover, many wish to compare the infection rates of several hospitals. However, this lack of objectivity makes such comparisons unreliable.

III. SUMMARY

The method for identifying hospital-acquired infections that is the subject of this patent solves the limitations of the current state of the art. This method is an electronic measurement of existing hospital data that is capable of surveying the entire hospital population. It does not require the extensive manual labor of the current state of the art. Also unlike the current state of the art, it is objective and reproducible. By applying the same criteria to each patient record and hospital, different people applying this method to the same data set would arrive at the same measurement.

This method utilizes laboratory results, pharmacy data and patient admit-transfer-discharge data that nearly every hospital has in electronic format. Using the described method, one is able to compute the number of Nosocomial Infection Markers (NIM). Clinical studies have shown that the number of NIMs corresponds to the number of distinct hospital-acquired infections—thereby serving as a clinically valid proxy measure. Financial studies have demonstrated that each NIM is correlated with 7.5 extra days stay in the hospital and $14,000 in variable treatment cost (risk-adjusted). Thus, the Method can also be used to predict the length of stay and cost implications of hospital-acquired infections.

IV. BRIEF DESCRIPTION OF THE DRAWINGS

The accompanying drawings, which are incorporated in and constitute a part of this specification, illustrate several embodiments and together with the description illustrate the disclosed compositions and methods:

V. DETAILED DESCRIPTION OF THE PREFERRED EMBODIMENT

Figure 1:
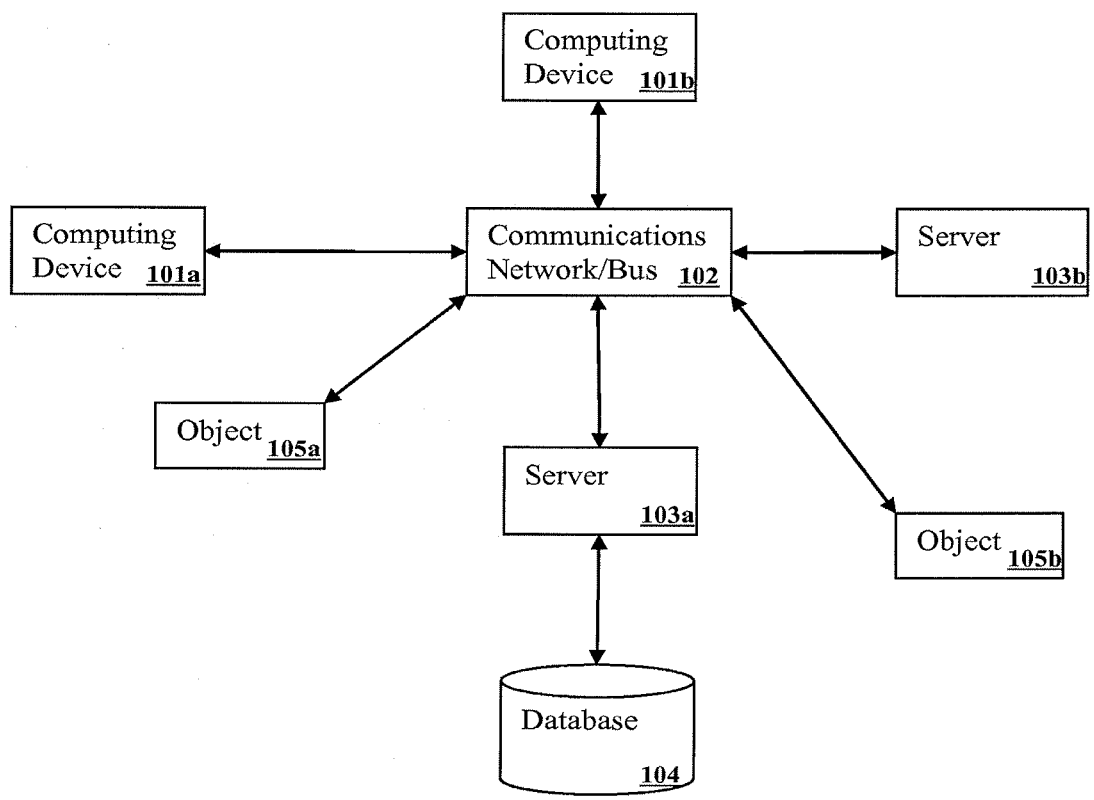
FIG. 1 is a block diagram representing an exemplary network environment having a variety of computing devices in which the present invention may be implemented.

Before the present methods are disclosed and described, it is to be understood that the terminology used herein is for the purpose of describing particular embodiments only and is not intended to be limiting. The term "computer-readable medium" encompasses distribution media, intermediate storage media, execution memory of a computer, and any other medium or device capable of storing for later reading by a computer a computer program implementing the method of this invention. Computer programs implementing the method of this invention will commonly be distributed to users on a distribution medium such as floppy disk or CD-ROM. From there, they will often be copied to a hard disk or a similar intermediate storage medium. When the programs are to be run, they will be loaded either from their distribution medium or their intermediate storage medium into the execution memory of the computer, configuring the computer to act in accordance with the method of this invention. All these operations are well-known to those skilled in the art of computer systems.

A. DEFINITIONS

As used in the specification and the appended claims, the singular forms "a," "an" and "the" include plural referents unless the context clearly dictates otherwise. Thus, for example, reference to "an infection" includes mixtures of two or more such infections, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Nosocomial Infection," (NI) also known as "Hospital-acquired Infection," is a localized or systemic condition that results from adverse reaction to the presence of an infectious agent(s) or its toxin(s) and that was not present or incubating at the time of admission to the hospital or hospital-like facility but rather was acquired during a hospital or facility encounter.

"Nosocomial Infection Marker" (NIM) is a value associated with the occurrence of a distinct nosocomial infection.

"Isolate" is a microorganism (bacteria, virus, fungus, yeast, parasite, protozoa) or evidence of the presence of a microorganism (e.g. DNA, serology, histology, microscopy) identified in the laboratory analysis of a specimen.

"Hospitalization" is the condition of being treated as a patient in a hospital or hospital-like facility for any length of time.

"Hospital" is any facility at which a patient can receive medical attention.

"Class of patient" is any group of patients that are linked by a common feature. Such features can include, but are not limited to, diagnosis, service provider, location in hospital, physician, and age. Other features are known to those skilled in the art and are herein specifically contemplated.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. EXEMPLARY NETWORKED AND DISTRIBUTED ENVIRONMENTS

One of ordinary skill in the art can appreciate that a computer or other client or server device can be deployed as part of a computer network, or in a distributed computing environment. In this regard, the present invention pertains to any computer system having any number of memory or storage units, and any number of applications and processes occurring across any number of storage units or volumes, which may perform operations in connection with NIM calculation. The present invention may apply to an environment with server computers and client computers deployed in a network environment or distributed computing environment, having remote or local storage. The present invention may also be applied to standalone computing devices, having programming language functionality, interpretation and execution capabilities for generating, receiving and transmitting information in connection with remote or local services.

FIG. 1 provides a schematic diagram of an exemplary networked or distributed computing environment. The distributed computing environment comprises computing objects 105a, 105b, etc. These objects may comprise programs, methods, data stores, programmable logic, etc. Each object can communicate with another object by way of the communications network 102. This network may itself comprise other computing objects and computing devices that provide services to the system of FIG. 1. In accordance with an aspect of the invention, each object 105 or device 101 may contain an application that might request NIM calculation resources of a host system.

Thus, FIG. 1 illustrates an exemplary networked or distributed environment, with a server in communication with client computers via a network/bus, in which the present invention may be employed. In more detail, a number of servers 103a, 103b, etc., are interconnected via a communications network/bus 102, which may be a LAN, WAN, intranet, the Internet, etc., with a number of client or remote computing devices 101a, 101b, 101c, 101d, 101e, etc., such as a portable computer, handheld computer, thin client, networked appliance, or other device. A database 104 is depicted which can reside on a server 103a, 103b, etc. . . . or other computing device. Database 104 can be any form of data storage system including, but not limited to, a flat file, a relational database (SQL), and an OLAP database (MDX and/or variants thereof). It is thus contemplated that the present invention may apply to any computing device in connection with which it is desirable to provide improved NIM calculation.

C. EXEMPLARY COMPUTING DEVICE

Figure 2:
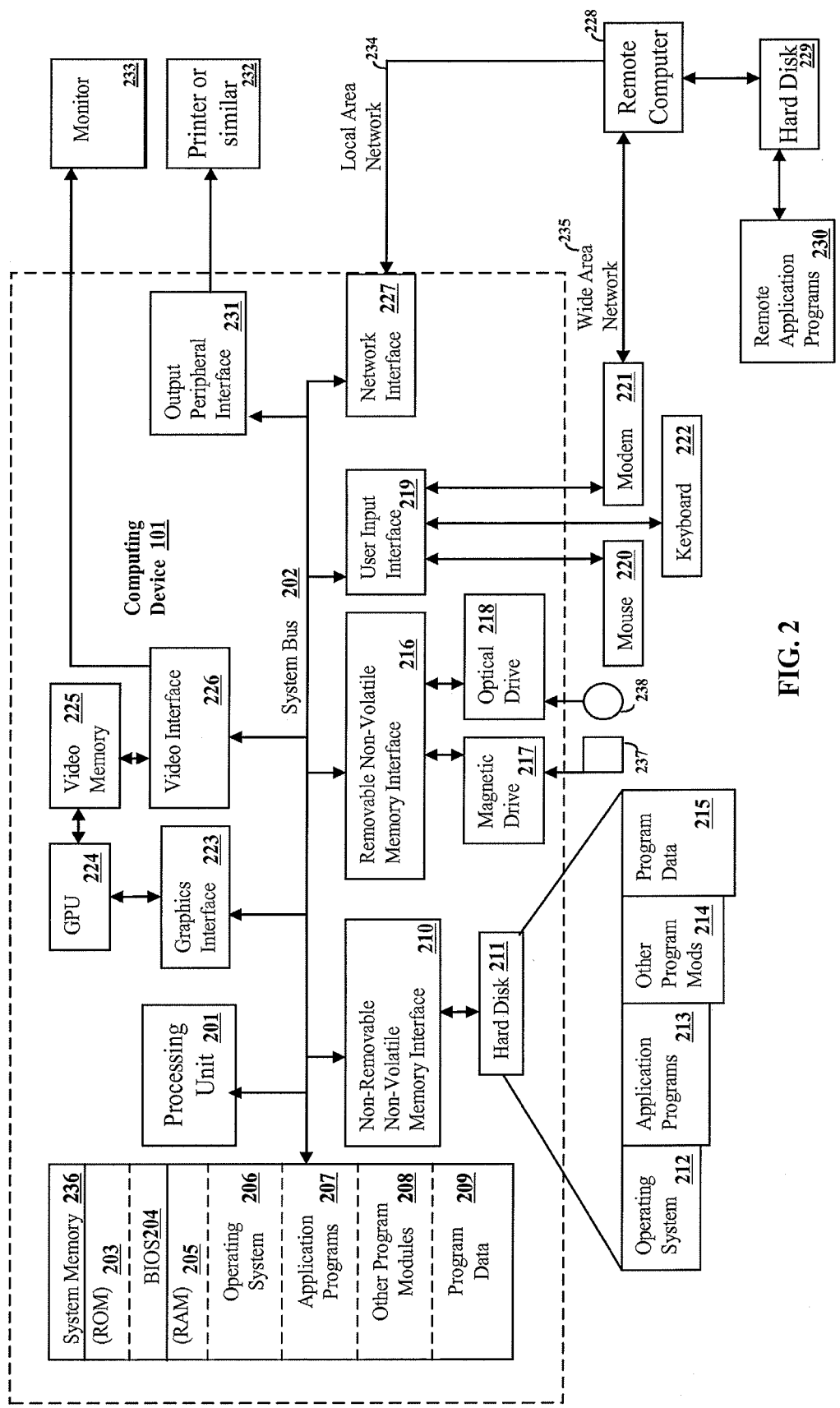
FIG. 2 is a block diagram representing an exemplary non-limiting computing device in which the present invention may be implemented.

FIG. 2 and the following discussion are intended to provide a brief general description of a suitable computing environment in which the invention may be implemented. It should be understood, however, that handheld, portable and other computing devices and computing objects of all kinds are contemplated for use in connection with the present invention. While a general purpose computer is described below, this is but one example, and the present invention may be implemented with a thin client having network/bus interoperability and interaction. Thus, the present invention may be implemented in an environment of networked hosted services in which very little or minimal client resources are implicated, e.g., a networked environment in which the client device serves merely as an interface to the network/bus, such as an object placed in an appliance. In essence, anywhere that data may be stored or from which data may be retrieved is a desirable, or suitable, environment for operation of the techniques of the invention.

Although not required, the invention can be implemented via an operating system, for use by a developer of services for a device or object, and/or included within application software that aids in performing NIM calculation. Software may be described in the general context of computer-executable instructions, such as program modules, being executed by one or more computers, such as client workstations, servers or other devices. Generally, program modules include routines, programs, objects, components, data structures and the like that perform particular tasks or implement particular abstract data types. Typically, the functionality of the program modules may be combined or distributed as desired in various embodiments. Moreover, those skilled in the art will appreciate that the invention may be practiced with other computer system configurations. Other well known computing systems, environments, and/or configurations that may be suitable for use with the invention include, but are not limited to, personal computers (PCs), server computers, hand-held or laptop devices, multi-processor systems, microprocessor-based systems, programmable consumer electronics, network PCs, minicomputers, mainframe computers and the like. The invention may also be practiced in distributed computing environments where tasks are performed by remote processing devices that are linked through a communications network/bus or other data transmission medium. In a distributed computing environment, program modules may be located in both local and remote computer storage media including memory storage devices and client nodes may in turn behave as server nodes.

FIG. 2 thus illustrates an example of a suitable computing system environment in which the invention may be implemented, although as made clear above, the computing system environment is only one example of a suitable computing environment and is not intended to suggest any limitation as to the scope of use or functionality of the invention. Neither should the computing environment be interpreted as having any dependency or requirement relating to any one or combination of components illustrated in the exemplary operating environment.

With reference to FIG. 2, an exemplary system for implementing the invention includes a general purpose computing device in the form of a computer 101. Components of computer 101 may include, but are not limited to, a processing unit 201, a system memory 236, and a system bus 202 that couples various system components including the system memory to the processing unit 201. The system bus 202 may be any of several types of bus structures including a memory bus or memory controller, a peripheral bus, and a local bus using any of a variety of bus architectures.

Computer 101 typically includes a variety of computer readable media. Computer readable media can be any available media that can be accessed by computer 101 and includes both volatile and nonvolatile media, removable and non-removable media. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can accessed by computer 101. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 236 includes computer storage media in the form of volatile and/or nonvolatile memory such as read only memory (ROM) 203 and random access memory (RAM) 205. A basic input/output system 204 (BIOS), containing the basic routines that help to transfer information between elements within computer 101, such as during start-up, is typically stored in ROM 203. RAM 205 typically contains data and/or program modules that are immediately accessible to and/or presently being operated on by processing unit 201. By way of example, and not limitation, FIG. 2 illustrates operating system 206, application programs 207, other program modules 208, and program data 209.

The computer 101 may also include other removable/non-removable, volatile/nonvolatile computer storage media. By way of example only, FIG. 2 illustrates a hard disk drive 211 that reads from or writes to non-removable, nonvolatile magnetic media, a magnetic disk drive 217 that reads from or writes to a removable, nonvolatile magnetic disk 237, and an optical disk drive 218 that reads from or writes to a removable, nonvolatile optical disk 238, such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 211 is typically connected to the system bus 202 through a non-removable memory interface such as interface 210, and magnetic disk drive 217 and optical disk drive 218 are typically connected to the system bus 202 by a removable memory interface, such as interface 216.

The drives and their associated computer storage media discussed above and illustrated in FIG. 2 provide storage of computer readable instructions, data structures, program modules and other data for the computer 101. In FIG. 2, for example, hard disk drive 211 is illustrated as storing operating system 212, application programs 213, other program modules 214, and program data 215. Note that these components can either be the same as or different from operating system 206, application programs 207, other program modules 208, and program data 209. Operating system 212, application programs 213, other program modules 214, and program data 215 are given different numbers here to illustrate that, at a minimum, they are different copies. A user may enter commands and information into the computer 101 through input devices such as a keyboard 222 and pointing device 220, commonly referred to as a mouse, trackball or touch pad. Other input devices (not shown) may include a microphone, joystick, game pad, satellite dish, scanner, or the like. These and other input devices are often connected to the processing unit 201 through a user input interface 219 that is coupled to the system bus 202, but may be connected by other interface and bus structures, such as a parallel port or a universal serial bus (USB). A graphics interface 223 may also be connected to the system bus 202. One or more graphics processing units (GPUs) 224 may communicate with graphics interface 223. A monitor 233 or other type of display device is also connected to the system bus 202 via an interface, such as a video interface 226, which may in turn communicate with video memory 225. In addition to monitor 233, computers may also include other peripheral output devices such as a printer 232, which may be connected through an output peripheral interface 231.

The computer 101 may operate in a networked or distributed environment using logical connections to one or more remote computers, such as a remote computer 228. The remote computer 228 may be a personal computer, a server, a router, a network PC, a peer device or other common network node, and typically includes many or all of the elements described above relative to the computer 101, although only a memory storage device 229 has been illustrated in FIG. 2. The logical connections depicted in FIG. 2 include a local area network (LAN) 234 and a wide area network (WAN) 235, but may also include other networks/buses.

When used in a LAN networking environment, the computer 101 is connected to the LAN 234 through a network interface or adapter 227. When used in a WAN networking environment, the computer 101 typically includes a modem 221 or other means for establishing communications over the WAN 235, such as the Internet. The modem 221, which may be internal or external, may be connected to the system bus 202 via the user input interface 219, or other appropriate mechanism. In a networked environment, program modules depicted relative to the computer 101, or portions thereof, may be stored in the remote memory storage device. By way of example, and not limitation, FIG. 2 illustrates remote application programs 230 as residing on memory device 229. It will be appreciated that the network connections shown are exemplary and other means of establishing a communications link between the computers may be used.

D. EXEMPLARY NIM CALCULATION INPUT DATA

The method relies on hospitalization data collected from electronic hospital information systems, including laboratory data collected from the laboratory information system and pharmacy ordering and dispensing data obtained from a pharmacy information system. Hospital patient census or Admit-Transfer-Discharge data can be obtained from one or more electronic hospital information systems. This data can be stored in light to heavy weight databases, in flat files or similar storage formats. Data can be extracted from client facilities on an ongoing basis using a secure, HIPAA-compliant method. This non-standard data can be cleaned and mapped into uniform data amenable to population-wide analysis.

By way of example, and not limitation, combinations of the following data can be used to form hospitalization data:

1. For each patient admit, discharge and transfer (ADT):
  a) Medical Record Number
  b) Admission date
  c) Transaction/ADT date
  d) Transaction type/Event (A, D, T, pre-admit, etc.)
  e) To Location (Ward)—admitted to, transferred to
  f) From Location (Ward)—transferred from, discharged from
  g) Site (facility) identifier, if applicable 2. For each and every microbiology and microbiology related test performed on the patients within the hospital:
  a) Facility Name/identifier
  b) Patient Medical record number (MR#)
  c) Encounter Date (e.g., Admission)
  d) Patient Location when specimen collected/resulted
  e) Source/Type of Specimen (e.g., Sputum, Blood, Urine)
  f) Date Specimen Collected
  g) Test Id/Name (e.g., ID & susceptibility, fungal culture, viral panel, C., difficile toxin)
  h) Isolate description (i.e., Microorganism name or description of evidence of the presence of a microorganism)
  i) Test Method (e.g. MIC, ETEST, Kirby-Bauer, EIA)
  j) Antibiotics (if applicable, >1 antibiotic per organism possible)
  k) Interpreted Result (if applicable, e.g., R-esistant, I-ntermediate, S-usceptible per antimicrobial)

3. For each patient hospitalization and antimicrobial dispensed:
  a) Medical Record Number
  b) Admission date
  c) Antimicrobial name, dose, route administered
  d) Date/time dispensed

E. NIM COMPUTATION

Values for the variables N, J, Y, K, X, Q, P, R, and S disclosed herein can be selected by one of skill in the art considering such variables as the type of facility, type of patients, type of diagnoses, type of infections, type of antimicrobial agents used, and other variables recognized by one of skill in the art.

Figure 3:
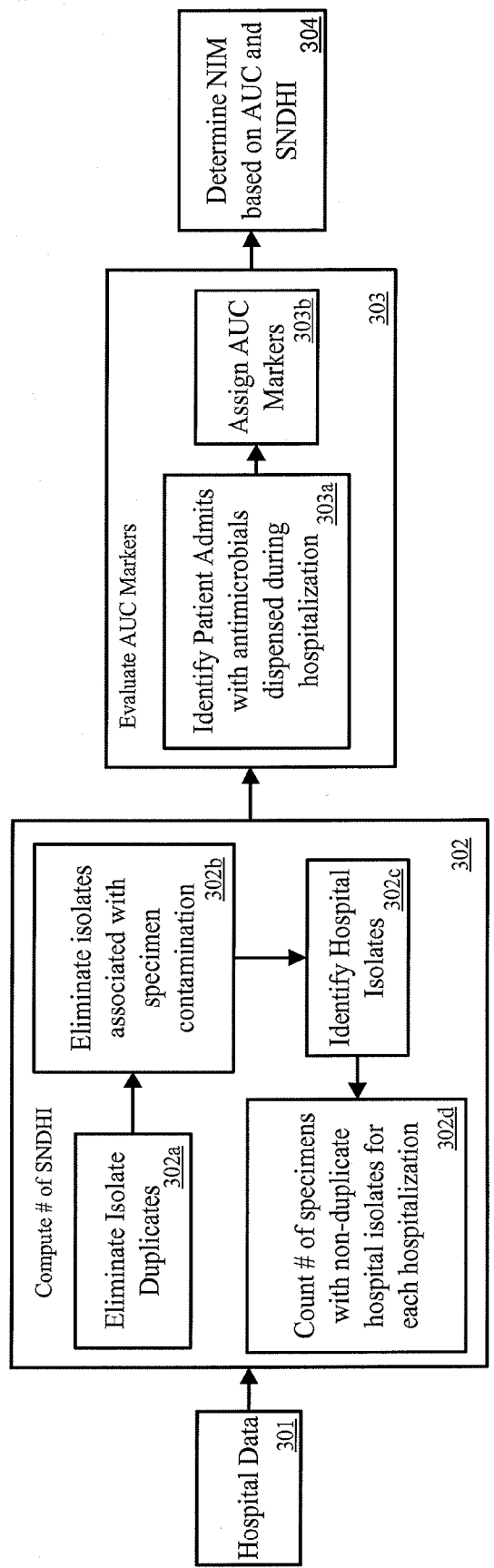
FIG. 3 is a block diagram representing the method of the present invention.

As seen in FIG. 3, the first step in NIM computation is to compute for each patient hospitalization the number of Specimens with Non-Duplicate Hospital Isolates (SNDHI) 302 from the hospital data received 301.

An "isolate" is a microorganism (bacteria, virus, fungus, yeast, parasite, protozoa) or evidence of the presence of a microorganism (e.g. DNA, serology, histology, microscopy) identified in the laboratory analysis of a specimen (patient fluid or tissue submitted for laboratory analysis). A specimen can yield zero or more isolates.

The first step in SNDHI computation 302 is to eliminate duplicate isolates 302a. This is done by segregating the first isolate of the same microorganism from the same patient obtained during an N-day period of time (N≥0), N can be selected for example, from 1-150 days or 25-50 days (N can be 30 days), not limited to the present admission. For each additional isolate of the same microorganism from the same patient obtained within N(N≥0) days of the first isolate, if the additional isolate is tested against one or more antimicrobial drugs and has interpreted antimicrobial susceptibility results that differ from the first isolate on fewer than J (J≥0), J can be, for example, selected from 1-20 or 1-10 (J can be 3), tested drugs, the additional isolate is a duplicate. For each additional isolate of the same microorganism (based, for example, on any indicator or indicators of the microorganism) obtained within N (N≥0) days of the first isolate, if the additional isolate is not tested against antimicrobial drugs, the additional isolate is a duplicate.

The second step in SNDHI computation is to eliminate isolates associated with specimen contamination, surveillance, and non-infected clinical states 302b. By way of example, and not limitation, isolates eliminated can include:
1) Coagulase-negative staphylococci, viridans group streptococci, and *Candida* species from respiratory specimens;
2) *Aspergillus* species from upper respiratory specimens;
3) Coagulase-negative *Staphylococcus* species, *Bacillus* species, *Corynebacteria* species, and diptheroids isolated only from broth or liquid laboratory culture media;
4) Isolate results in which no microorganism species is named (e.g. yeast, mixed flora);
5) Isolates obtained from decubitus specimens;
6) Isolates obtained from a specimen that yields>Y (Y>1), Y can be selected for example, from 1-20 or 1-10 (Y can be 2), isolates;
7) Isolates from surveillance specimens, i.e. specimens collected when no infection at the specimen source is suspected by a healthcare professional;
8) Isolates from bloodstream catheter tips that are not also obtained from blood cultures;
9) Isolates from environmental specimens;
10) Isolates from gynecology specimens, excluding surgical wounds;
11) Isolates from dermatology specimens; and
12) Urine isolates that yield fewer than 10,000 colonies/cc of urine.

The third step in SNDHI computation is to identify hospital isolates 302c. A "hospital isolate" can be an isolate obtained from a specimen collected from a patient during or after a hospitalization. A "hospital isolate" can be an isolate obtained from a specimen collected from a patient after being in the hospital for X consecutive days/hours, where X>0, and hospital day 0 is the day of admission. A "hospital isolate" can also be an isolate obtained from a specimen collected from a patient who has been a hospitalized patient one or more times within K days/hours prior to specimen collection, (K≥0). X can be selected, for example, from 1-20 hours or days or 1-10 hours or days. For example, X can be 2. K can be selected, for example, from 1-50 or 1-20 days/hours. For example, K can be 14 days. At this point, each "hospital isolate" identified is a SNDHI and each SNDHI is given the collected date of the specimen that yielded the hospital isolate.

In the fourth step of SNDHI computation, the sum of the computed SNDHI's can be calculated 302d.

The second step in NIM computation is to compute for each patient hospitalization Antibiotic Utilization Criteria (AUC) markers 303.

AUC computation comprises two steps:

Step 1. Identify episodes of antimicrobials dispensed during the course of hospitalization 303a.

Step 2. If the first episode of antibiotic dispensed occurred on hospital day Q>=R(R>0) and that at least one additional antibiotic episode occurred on a) each of the next S(S>0) days or b) the day of discharge or c) the day of death, assign one AUC marker to the hospitalization 303b and give it the date of Q. R can be selected for example, from 1-20 or 1-10, and S can be selected for example, from 2-20 or 2-10 consecutive days. R can be hospital day 3, and S can be 3.

The final step in NIM computation 304 is to compute for each admission the number of NIM by one of the formulae below:
1) NIM=SNDHI
2) NIM=AUC The NIM calculation formula selected can be selected by one of skill in the art considering such variables as the type of facility, type of patients, types of diagnoses, type of infections, types of antimicrobial agents used, and other variables recognized by one of skill in the art. Formula selection can depend on a preliminary evaluation of SNDHI and AUC and can be conditioned such that the selection of one formula for NIM calculation can depend on the evaluation of the other formula. For example, the selection of formula 2, NIM=AUC, can optionally depend on the preliminary evaluation of formula 1, NIM=SNDHI, and a certain result (e.g. 0) for formula 1. Likewise, the selection of formula 1, NIM=SNDHI, can optionally depend on the preliminary evaluation of formula 2, NIM=AUC, and a certain result (e.g. >0), and that the AUC occurred within P days/hours of a SNDHI.

The final NIM result can then be used for hospital quality benchmarking (ie., NIM's/total hospital admissions) and can also be used to assist hospitals developing a report of hospital-acquired infections to regulatory agencies. The final NIM result can also be used as an objective measure upon which to compare the relative performance among many hospitals and to objectively measure improvements or otherwise within a facility over time. The NIM result can be used as a measure of financial efficiency. The NIM result can allow hospitals to predict length of stay and cost implications associated with hospital-acquired infections. The NIM result can be used to reduce the number of hospital-acquired infections by identifying correctable process breakdowns causing infections, and focusing hospital staff on quality issues as they emerge.

The rate of NIMs across all admissions within a hospital divided by the number of admissions in that hospital over a given time period (e.g., one year) can be compared to the same rate at other hospitals, so as to provide an objective benchmarking measure of the hospital-wide incidence of nosocomial infection across multiple facilities.

The profit/loss of patients with one or more NIMs can be compared to the profit/loss of patients with no NIMs to measure the financial impact of hospital-acquired infections. Patterns of NIMs may be used to indicate a patient care process breakdown that is likely to cause nosocomial infections in the future.

VI. EXAMPLES

The following examples are put forth so as to provide those of ordinary skill in the art with a complete disclosure and description of how the methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

Calculation of SNDHI

Using the following criteria: (i) as to duplicate isolates, segregating the first isolate of the same microorganism from the same patient obtained during an N-day period of time (where N=30) and (ii) as to "hospital isolates," considering only those isolates obtained from a specimen collected from a patient after being in the hospital for X consecutive days/hours, where X=3 days, and hospital day 0 is the day of admission, here are some examples of SNDHI calculation:
SNDHI Example A:
  Day 0—Positive Urine—*E. coli*
  Day 1—No Cultures
  Day 2—No Cultures
  Day 3—Positive Blood—MSSA
  Day 4—Positive Blood—MSSA
  Day 5—No Cultures
  RESULT: 1 SNDHI
SNDHI Example B:
  Day 0—No Cultures
  Day 1—No Cultures
  Day 2—No Cultures
  Day 10—Positive Blood—Coag-neg *Staph*
  Day 14—Positive Resp—*Klebsiella* & Pseudom
  RESULT: 2 SNDHIs
SNDHI Example C:
  Day 0—Positive Nasal—Influenza
  Day 1—No Cultures
  Day 2—No Cultures
  Day 8—Positive Blood—MRSA
  Day 9—Positive Respiratory—MRSA
  Day 11—Positive Respiratory—*Klebsiella*
  RESULT: 2 SNDHIs

B. Example 2

Calculation of AUC

Using the following criteria: if antimicrobials were started on or after hospital day N, where N=3 days and were given for a) at least 4 consecutive days or b) until discharge or c) death, assign one AUC marker to the hospitalization, the following are examples of AUC calculation:
AUC Example A:
  Days 0 through 4: Azithromycin given
  Day 4: Patient discharged
  RESULT: 0 AUC
AUC Example B:
  Days 0 through 4: Azythromycin Zithromyacin prescribed given
  Day 10: Levofloxacinm given
  Day 14: —Patient discharged
  RESULT: 0 AUC
AUC Example C:
  Days 8 through 11: Imipenum given
  Day 11: —Patient dies
  RESULT: 1 AUC
AUC Example D:
  Days 8 through –15: Vancomycin given
  Days 40 through 45: Imipenem given
  Day 50—Patient discharged
  RESULT: 1 AUC

C. Example 3

Calculation of NIMs

NIM Example A: (Using MM Formula 1)
  Number of SNDHIs=2
  Number of AUC=0
  RESULT=2 NIMs
NIM Example B: (Using NIM Formula 1)
  Number of SNDHIs=3
  Number of AUC=1
  RESULT=3 NIMs
NIM Example C: (Using NIM Formula 2)
  Number of SNDHIs=2
  Number of AUC=1
  RESULT=1 NIM
NIM Example D: (Using MM Formulas 2)
  Number of SNDHIs=0
  Number of AUC=1
  RESULT=1 NIM
NIM Example E: (Using NIM formula 1 or 2)
  Number of SNDHIs=0
  Number of AUC=0
  RESULT=0 NIMs

D. Example 4

Evanston Northwestern Healthcare (ENH) is a three hospital, university-affiliated system comprised of two community hospitals and one tertiary-care referral hospital with more than 41,000 combined inpatient admissions annually. Consecutive admissions to ENH for Dec. 1 through 3, 2003 (n=507) and Apr. 26 through 29, 2004 (n=400) were assessed for development of Nosocomial Infection (NI) within 30 days of admission by comprehensive review of electronic medical records and by NIM analysis. The two time periods were specifically selected to represent distinct parts of the calendar year.

Nosocomial infections were defined according to published CDC criteria. An Intensive Care Unit (ICU)-associated NI was defined as an NI that develops on or after the third day of an ICU stay or within 3 days of leaving an ICU. As in the Study on the Efficacy of Nosocomial Infection Control (SENIC), the percentage of admissions with one or more NI was defined as the infection percentage and the total NI to total admissions ratio ×100 was defined as the infection ratio (Haley et al., *The SENIC Project. Study on the efficacy of nosocomial infection control*, 1980).

All medical records were available electronically. For NIM analysis, all positive final clinical microbiology and infectious disease-associated serology and molecular testing results were electronically collected on a daily prospective basis from the ENH laboratory information system. Additionally, the inpatient census was electronically collected every two hours so that patient movement through the hospital system could be determined.

A NIM was defined as a patient specimen with a non-duplicate hospital isolate, where a specimen can be a collection of material obtained from a single source (e.g. blood, urine, sputum, wound). A non-duplicate isolate can be the first direct or indirect identification of a microorganism from any specimen from the patient in the previous 30 days. A non-duplicate hospital isolate can be a non-duplicate isolate obtained from a specimen collected on or after hospital day 3 or within 14 days of hospital discharge (30 days for surgical wound specimens). If two isolates of the same microorganism are obtained from specimens collected within 30 days of each other and both are tested against antimicrobial agents, then the isolate from the latter specimen can be a non-duplicate only if its interpreted susceptibility results differ on more than two antimicrobials from the susceptibility results of the first isolate. Otherwise, it can be a duplicate. Results likely associated with specimen contamination and other non-infected clinical states were excluded before non-duplicate isolates were identified.

Medical records review and NIM analysis were done by separate investigators whose findings remained undisclosed until all possible NI were identified. Agreement between the two methods was considered definitive. Therefore, a possible NI identified by both medical records review and NIM analysis was considered a confirmed NI. Likewise, an admission without a possible NI by medical records review and NIM analysis was considered negative for NI. Discrepant cases were reviewed by two infectious disease (ID) physicians whose consensus decision was considered definitive. Expert chart review of discrepant possible NI has precedent in the evaluation of NNIS criteria, and expert epidemiologist-physician identification of NI was the reference standard to which the SENIC chart review NI identification methods were compared. Medical records review was performed by an ID physician and two medical technologists with clinical microbiology research expertise. Another ID physician provided direction and oversight and participated in discrepancy resolution. Each study admission had 0, 1, or more NIM, and 0, 1, or more NI.

Times per admission for the comprehensive review of electronic medical records were recorded during the review of the first admission set. All activities related to this study were approved by the ENH Institutional Review Board.

Comprehensive medical records review identified 45 possible NI in 40 admissions (infection percentage (IP)=4.4%, infection ratio (IR)=5.0). NIM analysis identified 60 possible NI in 47 admissions (IP=5.2%, IR=6.6), and 6 possible NI after the 30-day post-admission cut-off. Comparison of all possible NI identified by the two strategies yielded 25 discrepancies. After discrepancy resolution, a confirmed 49 NI in 44 admissions (IP=4.9%, IR=5.4) were identified. The sensitivity and specificity of medical records review were 0.92 and 1.0, respectively. The sensitivity and specificity of NIM analysis were 0.86 and 0.984, respectively.

From 142 admissions with an ICU component, NIM analysis identified 13 possible ICU-associated NI and medical records review identified 11 possible ICU-associated NI. Discrepancy resolution confirmed all 11 possible NI (1 bloodstream infection, 4 pneumonias, 6 urinary tract infections) identified by medical records review (sensitivity 1.0, specificity 1.0) and 11 of 13 possible NI identified by NIM analysis (sensitivity 1.0, specificity 0.986).

Targeted prospective surveillance by hospital Infection Control, as is now the standard practice for most U.S. hospitals, detected a total of 6 NI in 6 patients during the two study periods.

NIM analysis did not detect seven confirmed NI (4 wound infections, 1 pneumonia, 1 *Clostridium difficile*-associated diarrhea, 1 endometritis). Six of these had no corroborating microbiology data. Four of the six were from uncultured surgical wound infections (2 cesarean section delivery wounds, 1 breast biopsy wound, and 1 post-operative abdominal wound). One additional *C. difficile*-associated diarrhea was not detected due to a laboratory information system reporting error and one bacteremia could not be resolved by expert review. Both were excluded from analysis. NIM analysis correctly detected four NI (1 *C. difficile*-associated diarrhea, 1 bloodstream infection, 1 pneumonia, 1 urinary tract infection) in four admissions that were originally missed by medical records review. NIM analysis also identified 14 possible NI that were not NI on discrepancy resolution.

The manual review of electronic medical records required an average of 17 minutes per admission, or approximately 1.5 dedicated full-time employees per 10,000 yearly admissions. NIM analysis required approximately 10 minutes of personnel time per week to maintain and quality test the ongoing data transfer mechanism, or approximately two hours per 10,000 admissions.

VII. REFERENCES

1. Garner J S, et al. CDC definitions for nosocomial infections. In: Olmsted R N, ed.: *APIC Infection Control and Applied Epidemiology: Principles and Practice*. St. Louis: Mosby; 1996: pp. A-1-A-20.
2. Gavin P J, et al. Comparison of 'Whole House' Versus Routine Targeted Surveillance for Detection of Nosocomial Infection. *SHEA* 2004.
3. National Nosocomial Infections Surveillance (NNIS) System Report, Data Summary from January 1990-May 1999, Issued June 1999. *Am J Infect Control* 1999; 27:520-32.
4. Emori, et al. Accuracy of reporting nosocomial infections in intensive care unit patients to the national nosocomial infections surveillance system: a pilot study. *Infect Control Hosp Epidemiol* 1998; 19:308-316.
5. Haley R W, Quade D, Freeman H E, Bennett J V. The SENIC Project. Study on the efficacy of nosocomial infection control (SENIC Project). Summary of study design. Am J Epidemiol. May 1980; 111(5):472-485.

The invention claimed is:
1. A computer-readable, nonvolatile medium having computer-executable instructions stored thereon for execution by a processor to perform a method comprising the steps of:
receiving from a database hospitalization data associated with at least one patient;
identifying from the hospitalization data a day upon which a patient was admitted to the hospital and defining the day of admission as day 0;
identifying from the hospitalization data a day upon which antimicrobials were first dispensed to the patient and defining the day of first dispense as day Q;
identifying from the hospitalization data a number of days consecutively subsequent to day Q upon which the antimicrobials were dispensed to the patient and defining the number of consecutively subsequent days as C;

identifying whether the C consecutively subsequent days comprise at least one of a day of discharge from the hospital and a day of death of the patient; and assigning an Antibiotic Utilization Criteria (AUC) marker of one to the patient if day Q is at least R days after day 0, and either C is greater than or equal to S or the C consecutively subsequent days comprise at least one of the day of discharge and the day of death.

2. The computer-readable, nonvolatile medium of claim 1, wherein R and S are integers greater than zero.

3. The computer-readable, nonvolatile medium of claim 1, further comprising the step of:

setting a value of a Nosocomial Infection Marker (NIM) to be equal to the value of the AUC marker.

4. The computer-readable, nonvolatile medium of claim 1, wherein the hospitalization data are laboratory data.

5. The computer-readable, nonvolatile medium of claim 1, wherein the hospitalization data are pharmacy ordering and dispensing data.

6. The computer-readable, nonvolatile medium of claim 1, wherein the hospitalization data are patient census data.

7. The computer-readable, nonvolatile medium of claim 1, wherein the hospitalization data are Admit-Transfer-Discharge data.

8. The computer-readable, nonvolatile medium of claim 3, further comprising the step of:

displaying the NIM value.

9. The computer-readable, nonvolatile medium of claim 3, further comprising the step of:

outputting the NIM value to an output device.

* * * * *